US008557523B2

(12) United States Patent
Yonekawa et al.

(10) Patent No.: US 8,557,523 B2
(45) Date of Patent: Oct. 15, 2013

(54) METHOD OF NUCLEIC ACID AMPLIFICATION AND MEASURING REAGENT AND REAGENT KIT THEREFOR

(75) Inventors: Toshihiro Yonekawa, Otawara (JP); Tsugunori Notomi, Otawara (JP); Hidetoshi Kanda, Otawara (JP); Norimitsu Hosaka, Otawara (JP)

(73) Assignee: Eiken Kagaku Kabushiki Kaisha, Tokyo (JP)

( * ) Notice: Subject to any disclaimer, the term of this patent is extended or adjusted under 35 U.S.C. 154(b) by 574 days.

(21) Appl. No.: 12/738,413

(22) PCT Filed: Oct. 17, 2008

(86) PCT No.: PCT/JP2008/068829
§ 371 (c)(1),
(2), (4) Date: Apr. 16, 2010

(87) PCT Pub. No.: WO2009/051214
PCT Pub. Date: Apr. 23, 2009

(65) Prior Publication Data
US 2010/0233715 A1 Sep. 16, 2010

(30) Foreign Application Priority Data

Oct. 19, 2007 (JP) .................................. 2007-271902

(51) Int. Cl.
*C12Q 1/68* (2006.01)
*C07H 21/04* (2006.01)

(52) U.S. Cl.
USPC ........................................ 435/6.12; 536/24.3

(58) Field of Classification Search
None
See application file for complete search history.

(56) References Cited

U.S. PATENT DOCUMENTS

2006/0121516 A1* 6/2006 Norman et al. ................... 435/6

FOREIGN PATENT DOCUMENTS

| CN | 1687454 A | 10/2005 |
| WO | 03/089669 A1 | 10/2003 |
| WO | WO 2006/034215 A2 | 3/2006 |
| WO | WO 2007/059179 A1 | 5/2007 |

OTHER PUBLICATIONS

Heid et al. Real time quantitative PCR. Genome Research 6:986-994 (1996).*
Lund et al. Strategies for the inclusion of an internal amplification control in conventional and real time PCR detection of *Campylobacter* spp. in chicken fecal samples. Molecular and Cellular Probes 20:92-99 (2006).*
Coyne et al. Improved quantitative real-time PCR assays for enumeration of harmful algal species in field samples using an exogenous DNA reference standard. Limnology and Oceanography: Methods 3:381-391 (2005).*
Chinese Application No. 200880122150.2, Office Action dated Aug. 24, 2011.
Hoorfaf, J., et al., Practical Considerations in Design of Internal Amplification Controls for Diagnostic PCR Assays, Journal of Clinical Microbiology, 2004, 42(5):1863-1868.
European Patent Application No. 08 839 845.8, Communication pursuant to Article 94(3) EPC dated Mar. 14, 2012.
Anonymous, "Taqman Exogenous Internal Positive Control Reagents", Applied Biosystems: 2007, Molecular and Cell Biology Catalogue, 125 (2006).
Lo, Chung-Yau, et al., "High Prevalence of Cyclooxygenase 2 Expression in Papillary Thyroid Carcinoma", European Journal of Endocrinology, 152:545-550 (2005).
Su, Yan Ru, et al., "Rapid Quantification of Murine ABC mRNAs by Real Time Reverse Transcriptase-Polymerase Chain Reaction", Journal of Lipid Research, 43:2180-2187 (2002).
Hartman, Laurie J., et al., "Development of a Novel Internal Positive Control for Taqman® Based Assays", Molecular and Cellular Probes, 19:51-59 (2005).
Nurmi, J., et al., High-Performance Real-Time Quantitative RT-PCR Using Lanthanide Probes and a Dual-Temperature Hybridization Assay, Anal. Chem. 2002, 74:3525-3532.
European Application No. 08 839 845.8, Communication pursuant to Article (94(3) EPC dated Oct. 10, 2011.
Brightwell, G., et al., Development of Internal Controls for PCR Detection of *Bacillus anthracis*, 1998, Molecular and Cellular Probes, 12:367-377.
Tani, H., et al., Technique for Quantitative Detection of Specific DNA Sequences Using Alternately Binding Quenching Probe Competitive Assay Combined with Loop-Mediated Isothermal Amplification, 2007, Anal. Chem., 79:5608-5613.
European Communication Pursuant to Article 94(3) EPC, dated May 23, 2011.

* cited by examiner

*Primary Examiner* — Samuel Woolwine
(74) *Attorney, Agent, or Firm* — Pillsbury Winthrop Shaw Pittman LLP

(57) ABSTRACT

The object of the present invention is to provide a method that allows stable amplification of an internal standard material while maintaining an accurate assay value for a target nucleic acid in a nucleic acid detection system involving the use of an internal standard material and a reagent kit used therefor. The present invention relates to a method for nucleic acid amplification comprising preventing an internal standard amplification product from affecting amplification reaction of a target nucleic acid by performing amplification of an internal standard material prior to amplification of the target nucleic acid in the method for amplifying a target nucleic acid in a sample using an internal standard material and a reagent and reagent kit used therefor.

7 Claims, 11 Drawing Sheets

METHOD OF NUCLEIC ACID AMPLIFICATION AND MEASURING REAGENT AND REAGENT KIT THEREFOR

This application is the National Phase of International Application No. PCT/JP2008/068829, filed Oct. 17, 2008 which designated the U.S. and that International Application was published under PCT Article 21(2) in Japanese, and claims priority to Japanese Application No. 2007-271902, filed Oct. 19, 2007, all of which applications are expressly incorporated herein by reference in their entirety.

TECHNICAL FIELD

The present invention relates to a method for amplifying a nucleic acid in a sample and a reagent used therefor. More particularly, the present invention relates to a method of amplification involving the use of an internal standard material.

BACKGROUND ART

A variety of methods for nucleic acid amplification have been developed as techniques that allow detection of very small amounts of nucleic acids in a sample. In particular, a method in which efficient isothermal amplification is carried out (e.g., the LAMP method) has been employed in a wide variety of testing fields as a technique that allows simple and rapid detection with the use of a cost-effective apparatus without a temperature control function.

The present inventors reported that nucleic acids could be quantified at a concentration range of $10^3$ to $10^9$ copies/test with the use of a LAMP detection system that does not involve the use of an internal standard material (Y. Mori, et al., Journal of Biochemical and Biophysical Methods, 59, 145-157, 2004). Since this technique does not use an internal standard material, the results obtained by such technique are relative amounts of target nucleic acids.

Meanwhile, a method of quantification involving the use of an internal standard material in the LAMP method was reported (H. Tani, et al., Analytical Chemistry, 79 (15), 5608-5613, 2007). This method involves the use of an internal standard material having a sequence similar to that of the target nucleic acid to simultaneously amplify the target nucleic acid and the internal standard material. Since the quantifiable concentration range of this method is as small as $10^4$ to $10^8$ copies/test, it is necessary to dilute a sample and repeat assays a plurality of times in order to assay nucleic acids of a wide concentration range.

DISCLOSURE OF THE INVENTION

In a detection system involving the use of an internal standard material, an amplification product of the internal standard material affects an amplification reaction of a target nucleic acid. Thus, a target nucleic acid cannot be accurately assayed, and such drawback is considered to be a common problem of isothermal nucleic acid amplification techniques that yield high amplification efficiency. The present invention is intended to overcome such drawback and to provide a method that allows stable amplification of an internal standard material while maintaining an accurate assay value for a target nucleic acid and a reagent used therefor.

The present inventors have conducted concentrated studies in order to attain the above object. As a result, they have found that the influence of an internal standard amplification product imposed on an amplification reaction of a target nucleic acid can be avoided by refraining from performing an amplification reaction of an internal standard material simultaneously with a reaction of a target nucleic acid; that is, by performing an amplification reaction of an internal standard material prior to or subsequent to a reaction of a target nucleic acid. This has led to the completion of the present invention.

Specifically, the present invention provides (1) to (9) below.

(1) A method for nucleic acid amplification comprising performing amplification of an internal standard material prior to amplification of a target nucleic acid.

(2) The method for nucleic acid amplification according to (1) comprising the steps of:

(a) adding a solution containing an internal standard material with a known concentration or copy number to a sample containing a target nucleic acid;

(b) performing an amplification reaction using an amplification reaction solution containing an oligonucleotide primer used for amplification of an internal standard material that allows performance of amplification of an internal standard material prior to amplification of a target nucleic acid (hereafter referred to as an "internal standard primer") and an oligonucleotide primer used for amplification of a target nucleic acid (hereafter referred to as a "target nucleic acid primer") under given conditions; and (c) performing assay via a means that allows the amplification reaction of the internal standard material to be distinguished from the amplification reaction of the target nucleic acid.

(3) The method for nucleic acid amplification according to (1) or (2), wherein the target nucleic acid is quantified.

(4) The method for nucleic acid amplification according to (1), comprising the steps of:

(a) adding a solution containing an internal standard material with a known concentration or copy number to a sample containing a target nucleic acid;

(b) performing an amplification reaction using an amplification reaction solution containing an oligonucleotide primer used for amplification of an internal standard material that allows performance of amplification of an internal standard material prior to amplification of a target nucleic acid (hereafter referred to as an "internal standard primer") and an oligonucleotide primer used for amplification of a target nucleic acid (hereafter referred to as a "target nucleic acid primer") under given conditions; and (c) performing real-time assay via a means that allows the amplification reaction of the internal standard material to be distinguished from the amplification reaction of the target nucleic acid and determining the initial concentration or copy number of the target nucleic acid in a sample based on the results of assay and the amount of the internal standard material added.

(5) The method for nucleic acid amplification according to any one of (1) to (4), wherein the internal standard material has a nucleotide sequence different from that of the target nucleic acid at least in the primer design region.

(6) The method for nucleic acid amplification according to (5), wherein the internal standard primer is designed to specifically hybridize to the internal standard material but not to hybridize to the target nucleic acid under given conditions and the target nucleic acid primer is designed to specifically hybridize to the target nucleic acid but not to hybridize to the internal standard material under the given conditions.

(7) The method for nucleic acid amplification according to (5) or (6), wherein the amplification reaction is the LAMP method.

(8) An assay reagent or reagent kit used for performing the method for nucleic acid amplification according to any one of (1) to (7).

(9) The assay reagent or reagent kit according to (8), which at least comprises the reagents described below:

(a) an internal standard material with a known concentration or copy number, which has a nucleotide sequence different from that of the target nucleic acid at least in the primer design region;

(b) an internal standard primer that allows performance of amplification of an internal standard material prior to amplification of the target nucleic acid under given conditions; and (c) a target nucleic acid primer.

According to the present invention, an amplification reaction of an internal standard material is performed prior to a reaction of a target nucleic acid, so that an internal standard material can be stably amplified while maintaining an accurate assay value for the target nucleic acid. According to qualitative techniques, specifically, the efficiency of extraction and purification from various samples or influence of components in samples on an amplification reaction can be monitored. According to quantification techniques, also, absolute amounts of nucleic acids can be assayed in a wide range of 7 digits or more.

Figure 1:
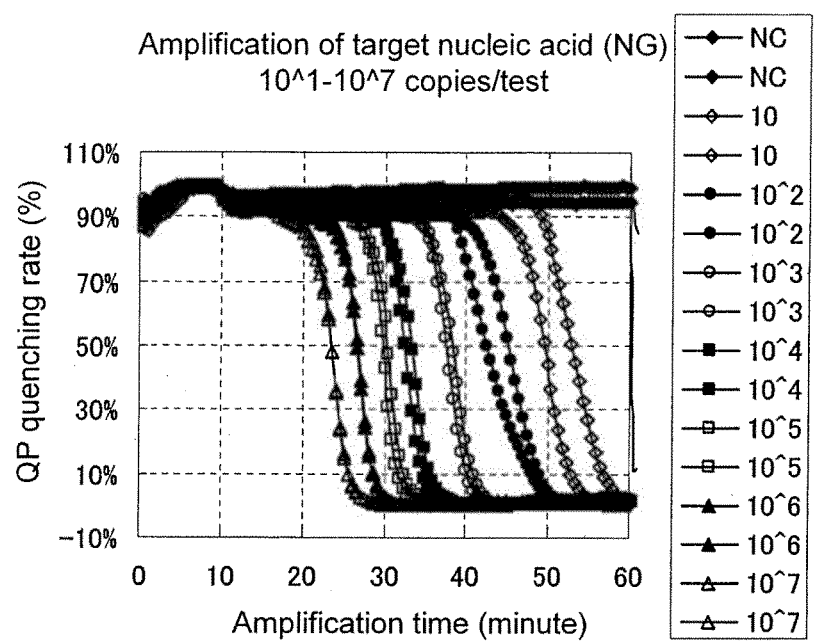
FIG. 1 is a chart showing the results attained via the LAMP method using a target nucleic acid (i.e., NG plasmid) at each concentration of $10^1$ to $10^7$ copies/test and an internal standard nucleic acid (i.e., CT plasmid) and assaying fluorescence quenching of a quenching probe caused along with amplification of the target nucleic acid via Mx3000P real-time assay.

This description includes the contents as disclosed in the specification of Japanese Patent Application No. 2007-271902, which is a priority document of the present application.

BEST MODES FOR CARRYING OUT THE INVENTION

The method for nucleic acid amplification of the present invention comprises performing amplification of an internal standard material prior to or subsequent to amplification of a target nucleic acid. The condition of amplification of an internal standard material being performed prior to amplification of a target nucleic acid means that an amplification reaction of the internal standard material is initiated before an amplification reaction of the target nucleic acid template is initiated. To this end, designing of an internal standard primer that allows performance of amplification with early timing (i.e., in advance) is necessary. The term "internal standard primer" refers to an oligonucleotide primer used for amplification of an internal standard material. In general, special conditions for designing a primer used to perform amplification with early timing have not yet been established. Thus, a primer used to perform amplification with early timing is selected from among primers that are designed by conventional techniques with the use of dedicated software or the like, and the selected primer is designated as an internal standard primer.

The condition of amplification of an internal standard material being performed subsequent to amplification of a target nucleic acid means that an amplification reaction of the internal standard material is initiated after an amplification reaction of the target nucleic acid template is initiated. To this end, designing of an internal standard primer that allows performance of amplification with late timing (i.e., afterward) is necessary. Thus, a primer used to perform amplification with late timing is selected from among primers that are designed by conventional techniques with the use of dedicated software or the like, and the selected primer is designated as an internal standard primer.

In a method for isothermal nucleic acid amplification, in general, the timing for amplification tends to be earlier as target nucleic acid concentration is elevated. Thus, it is necessary to elevate concentration of the internal standard material in order to amplify the internal standard material with early timing. In contrast, it is necessary to reduce concentration of the internal standard material in order to amplify the internal standard material with late timing.

In the present invention, specifically, the concentration of the internal standard material in the amplification reaction solution is set to be higher than that in the amplification reaction solution used for assay via simultaneous amplification of an internal standard material and the target nucleic acid, in order to amplify the internal standard material with early timing (i.e., in advance). Such concentration is preferably set to be 10 times as high or higher, and more preferably 100 times as high or higher. In contrast, concentration of the internal standard material in the amplification reaction solution is set lower than that in the amplification reaction solution used for assay via simultaneous amplification of an internal standard material and the target nucleic acid, in order to amplify the internal standard material with late timing (i.e., afterward). Such concentration is preferably set to be 0.1 times as low or lower, and more preferably 0.01 times as low or lower.

The internal standard material used in the present invention is not particularly limited, provided that the relevant nucleic acid has a nucleotide sequence different from that of the target nucleic acid at least in the primer design region. Examples of such nucleic acid include a naturally occurring nucleic acid and a partially or fully artificially synthesized nucleic acid.

By reducing concentration of the internal standard primer of the present invention to a level lower than a general level (i.e., a single nucleic acid detection system), the amount of the internal standard amplification product can be reduced, and accuracy of target nucleic acid assay can be improved. By elevating concentration of a substrate nucleotide for nucleic acid synthesis to a level higher than a general level, a substrate that is consumed in the amplification reaction of the internal standard material can be supplemented, and the problem of delay in target nucleic acid amplification can be resolved. This enables detection with higher sensitivity within a shorter period of time.

According to the present invention, specifically, concentration of the internal standard primer in the amplification reaction solution is set to be lower than that in the amplification reaction solution that is used for assay via simultaneous amplification of an internal standard material and the target nucleic acid, in order to amplify the internal standard material with early timing (i.e., in advance). Such concentration is set preferably 1 time lower, and more preferably 0.5 times or lower. Thus, the amount of the amplification product of the internal standard material can be reduced, and the accuracy of target nucleic acid assay can be improved.

In the present invention, further, concentration of a substrate nucleotide for nucleic acid synthesis is set to be higher than that in the amplification reaction solution that is used for assay via amplification of the same target nucleic acid without the use of an internal standard material, in order to amplify the internal standard material with early timing (i.e., in advance). Such concentration is set preferably higher than 1 time, and more preferably 1.1 times or higher. Thus, a substrate that is consumed in the amplification reaction of the internal standard material can be supplemented, and the problem of delay in target nucleic acid amplification can be resolved. This enables detection with higher sensitivity within a shorter period of time.

A person skilled in the art can adequately regulate the conditions for reaction reagent components described above, so as to amplify the internal standard material before the target nucleic acid.

The internal standard primer of the present invention is designed to specifically hybridize to the internal standard material but not to hybridize to the target nucleic acid under stringent conditions and the target nucleic acid primer is designed to specifically hybridize to the target nucleic acid but not to hybridize to the internal standard material under stringent conditions as described above.

Under stringent conditions, a specific hybrid is formed but a non-specific hybrid is not formed. Specifically, an oligonucleotide having high homology to a nucleic acid (i.e., homology of 80% or higher, preferably 90% or higher, and more preferably 95% or higher) undergoes hybridization. More specifically, hybridization is carried out in the presence of 0.5 to 1M NaCl at 42° C. to 68° C. in the presence of 50% formamide at 42° C., or in an aqueous solution at 65° C. to 68° C., followed by washing with the use of a 0.1× to 2×SSC solution at room temperature to 68° C.

In one embodiment, the method for nucleic acid amplification of the present invention comprises the steps of:

(a) adding a solution containing an internal standard material with a known concentration or copy number to a sample containing a target nucleic acid;

(b) performing an amplification reaction using an amplification reaction solution containing an oligonucleotide primer used for amplification of an internal standard material that allows amplification of the internal standard material with earlier timing (i.e., in advance) than the amplification of the target nucleic acid and an oligonucleotide primer used for amplification of a target nucleic acid; and (c) performing assay via a means that allows the amplification reaction of the internal standard material to be distinguished from the amplification reaction of the target nucleic acid.

In another embodiment, the method for nucleic acid amplification of the present invention comprises the steps of:

(a) adding a solution containing an internal standard material with a known concentration or copy number to a sample containing a target nucleic acid, (b) performing an amplification reaction using an amplification reaction solution containing an oligonucleotide primer used for amplification of an internal standard material that allows amplification of the internal standard material with earlier timing (i.e., in advance) than the amplification of the target nucleic acid and an oligonucleotide primer used for amplification of a target nucleic acid; and (c) performing real-time assay via a means that allows the amplification reaction of the internal standard material to be distinguished from the amplification reaction of the target nucleic acid, and determining the initial concentration or copy number of the target nucleic acid in a sample based on the results of assay and the amount of the internal standard material added.

Samples used in the present invention are not particularly limited, provided that samples can comprise nucleic acids. Examples thereof include specimens derived from organisms such as humans and other animals, specimens derived from plants, food, and environments, substances containing partially or fully artificially synthesized nucleic acids, and culture solutions thereof. Such samples may be subjected to pretreatment, such as isolation, extraction, concentration, or purification.

In the present invention, the term "target nucleic acid" refers to a nucleic acid to be detected that is subjected to amplification. The term "target sequence" refers to a target nucleotide sequence on the target nucleic acid. The target nucleic acid may be any nucleic acid to be amplified, without particular limitation. Examples of target nucleic acids include various types of genes of animals and plants, various virus genes, and various microorganism genes, such as bacteria, mold, and yeast genes, regardless of whether or not they are DNA or RNA. Target nucleic acids may be naturally occurring or artificially synthesized, and an example thereof is PNA. Also, examples include single-stranded nucleic acids and double-stranded nucleic acids. In the present invention, the term "template nucleic acid" refers to an original target of detection that comprises in its molecules a target sequence and serves as a base for primer design.

Prior to pretreatment such as isolation, extraction, concentration, or purification, the internal standard material is added to the sample, the resultant is subjected to pretreatment, and the target nucleic acid is then assayed by the method of the present invention. Thus, efficiency of pretreatment can be monitored. When the internal standard material is added to a sample that had been subjected to pretreatment and target nucleic acids are qualitatively assayed, influence of components in the sample on the amplification reaction can be inspected, and a false negative reaction can be distinguished. Further, a variety of target nucleic acids with known concentrations may be subjected to the method of the present invention to prepare a standard curve in advance, and the results of assay of unknown test samples are compared with the resulting standard curve. Thus, the target nucleic acids in the unknown test samples can be quantified.

In the present invention, a method for detecting a nucleic acid is not particularly limited, provided that such method allows the amplification reaction of the internal standard material to be distinguished from the amplification reaction of the target nucleic acid. For example, methods involving the use of a fluorescence-labeled probe or radioactively labeled probe can be employed.

In the present invention, the method for nucleic acid amplification is not particularly limited, provided that it is a method for isothermal nucleic acid amplification that yields high amplification efficiency. For example, an amplification technique involving the use of a primer having the X1c+X2 structure; i.e., the loop-mediated isothermal amplification (LAMP) method, is preferable.

Hereafter, an amplification technique involving the use of a primer having the X1c+X2 structure is described. Specifically, a primer having the X1c+X2 structure is designed as follows:

(a) when a first arbitrary sequence F1c and a second arbitrary sequence F2c are successively selected from the 3' side of the target sequence on a template nucleic acid strand toward the 3' terminal on the template nucleic acid strand, a primer comprising a sequence identical to F1c and a sequence F2 complementary to F2c in that order from the 5' side toward the 3' side; and (b) when a third arbitrary sequence R1 and a fourth arbitrary sequence R2 are successively selected from the 5' side of the target sequence on a template nucleic acid strand toward the 5' terminal on the template nucleic acid strand, a primer comprising a sequence R1c complementary to R1 and sequence R2 identical to R2 in that order from the 5' side toward the 3' side.

The primers (a) and (b) may be used as a pair. Alternatively, either primer (a) or (b) may be used as a pair in combination with a general primer.

An amplification reaction can be carried out using a strand displacement-type DNA polymerase as a polymerase under isothermal conditions. This is because a primer has an X1c+X2 structure, an extension product from the primer comprises a complementary sequence (underlined) of X1c+(X2+)X1, and the extension product undergoes intrastrand annealing and forms a single-stranded region on the synthesized double-stranded nucleic acid. Specifically, a new origin for strand displacement is provided on an extension product via intrastrand annealing without dissociating the double strand at high temperature. Regarding the outline of this reaction, reference may be made to the description on the LAMP method below.

Examples of strand displacement-type DNA polymerase described above include Bst DNA polymerase, Bca(exo-) DNA polymerase, Klenow fragment of *E. coli* DNA polymerase I, Vent DNA polymerase, Vent(Exo-) DNA polymerase (resulting from removal of exonuclease activity from Vent DNA polymerase), DeepVent DNA polymerase, Deep-Vent(Exo-) DNA polymerase (resulting from removal of exonuclease activity from DeepVent DNA polymerase), Φ29 phage DNA polymerase, MS-2 phage DNA polymerase, Z-Taq DNA polymerase (Takara Shuzo Co., Ltd.), and KOD DNA polymerase (Toyobo Co., Ltd.).

The LAMP method is described below. The "LAMP method" was developed by Notomi et al. (Nucleic Acids Research, 28 (12), e63, 2000), and it is a method for nucleic acid amplification that enables isothermal complementary strand synthesis in which the template nucleotide is annealed to the 3' terminal thereof, the annealed site is used as an origin for complementary strand synthesis, and a primer that anneals to the resulting loop is used in combination. According to the LAMP method, the 3' terminal of the primer always anneals to a region derived from a sample. Thus, a checking mechanism resulting from a complementary bond of nucleotide sequences repeatedly functions. This enables amplification reaction of gene sequences with high specificity.

In the LAMP method, primers comprising at least 4 types of oligonucleotides that recognize nucleotide sequences in 6 regions in total on a nucleotide sequence of the template nucleic acid (an "inner primer F" (hereafter referred to as "FIP"), inner primer B (hereafter referred to as "BIP"), outer primer F (hereafter referred to as "F3"), and outer primer B (hereafter referred to as "B3")) are used. As the amplification reaction proceeds, a dumbbell-shaped nucleotide having a 3' terminal that serves as an origin for self-template synthesis and loop structures at both terminals is formed. When primers having a nucleotide sequence complementary to a nucleotide sequence in the single-stranded region of the 5' terminal loop structure of the dumbbell structure (i.e., a loop primer F (hereafter referred to as "LF") and/or a loop primer B (hereafter referred to as "LB")) are used, further, the number of origins for nucleic acid synthesis is increased, and this can shorten the reaction time and improve detection sensitivity.

An inner primer is necessary to carry out the LAMP method. When an arbitrary sequence X2c located on the 3' side and an arbitrary sequence X1c located closer to the 5' side in each template DNA strand are selected, an inner primer comprises a sequence X2 complementary to the sequence X2c and a sequence X1c identical to the sequence X1c from the 3' side toward the 5' side in that order (i.e., an inner primer has the X1c+X2 structure). In terms of functions, X2 of the inner primer anneals specifically to the template and provides an origin for complementary strand synthesis, and X1c provides a complementary sequence for an amplification (extension) product to form a loop. The resulting loop serves as a new origin for complementary strand synthesis.

The term "outer primer" refers to two types of primers (a primer complementary to each of double strands) having a sequence complementary to an arbitrary sequence X3c located outside of the inner primer (i.e., closer to the 3' side of the template) and capable of annealing thereto.

In order to facilitate annealing of a primer to a template nucleic acid, the lengths of the sequences X1 (X1c), X2 (X2c), and X3 (X3c) are each preferably 5 to 100 nucleotides, and more preferably 10 to 50 nucleotides.

The inner primer and the outer primer are necessary for each of double strands (F and R), and two types of inner primers (F1c+F2 and R1c+R2) and two types of outer primers (F3 and R3) are designed.

Arbitrary sequences are preferably selected, so that the amplification product resulting from the LAMP method preferentially causes intramolecular annealing, instead of intermolecular annealing, and forms a terminal hairpin structure. In order to preferentially cause intramolecular annealing, for example, it is important to take the distance between the sequence F1c and the sequence F2c and the distance between the sequence R1 and the sequence R1c into consideration when selecting arbitrary sequences. More specifically, sequences are selected, so that the distance therebetween is 0 to 500 nucleotides, preferably 0 to 100 nucleotides, and most preferably 10 to 70 nucleotides. The numerical values represent the number of nucleotides excluding the sequences F1c, F2c, R1, and R2.

The term "loop primer" refers to two types of primers (each primer being complementary to each of double strands) comprising at the 3' terminal a nucleotide sequence complementary to a sequence in a loop formed via annealing of complementary sequences generated on the same strand of an amplification product of the LAMP method. The outer primer and the loop primer are not indispensable for the LAMP method; however, use of these primers enables a more efficient amplification (extension) reaction.

A sequence of reactions is preferably carried out in the presence of a buffer that allows a preferable pH level in the enzyme reaction, a salt that is necessary for maintaining catalyst activity of an enzyme or for annealing, an enzyme protecting agent, and, according to need, a melting temperature (Tm) regulator. A buffer that has buffering actions under neutral-to-weak alkaline conditions, such as Tris-HCl, is used. The pH level may be adjusted in accordance with the type of DNA polymerase used. As a salt, for example, KCl, NaCl, $MgCl_2$, or $(NH_4)_2SO_4$, is added, so as to maintain enzyme activity and to modify melting temperature (Tm) of DNA, according to need. As an enzyme protector, bovine serum albumin or sugar is used. As a melting temperature (Tm) regulator, in general, betaine, proline, dimethyl sulfoxide, or formamide can be used.

The LAMP reaction proceeds by adding the components (i), (ii), and (iii) below to the template nucleic acid and performing incubation at temperature at which an inner primer is able to form a stable nucleotide pair bond with a complementary sequence on the template nucleic acid and strand-displacement type polymerase is able to maintain enzyme activity. Incubation is carried out at 50° C. to 75° C., and preferably 55° C. to 70°, for 1 minute to 10 hours, and preferably 5 minutes to 4 hours.

(i) Two types of inner primers, or further two types of outer primers, or further two types of loop primers;

(ii) Strand-displacement type polymerase;

(iii) Substrate nucleotide.

Nucleotide strand synthesis from the outer primer needs to be initiated after nucleotide strand synthesis from the inner primer is initiated. To this end, inner primer concentration is set to be higher than outer primer concentration, for example. Specifically, inner primer concentration may be set to be 2 to 50 times, and preferably 4 to 25 times, higher than the outer primer concentration.

Various reagents that are necessary when carrying out the method of the present invention can be packaged in advance to prepare a kit. For example, necessary reagents, such as an internal standard material, an internal standard primer, a target nucleic acid primer, four types of dNTPs that serve as substrates for nucleic acid synthesis, DNA polymerase, reverse transcriptase, buffer, salt, protector, and label probe, are provided in the form of a kit.

Specifically, the assay reagent or reagent kit of the present invention includes at least the reagents below:

(a) an internal standard material with a known concentration or copy number having a nucleotide sequence different from that of a target nucleic acid at least in the primer design region;

(b) an oligonucleotide primer used for amplification of an internal standard material that allows performance of amplification of an internal standard material prior to amplification of the target nucleic acid; and (c) an oligonucleotide primer used for amplification of a target nucleic acid.

The assay reagent or reagent kit of the present invention may further include the reagents below:

(a) an oligonucleotide probe used for detecting an internal standard material; and (b) an oligonucleotide probe used for detecting a target nucleic acid.

EXAMPLES

Examples of the present invention are described below, although the present invention is not limited to these examples.

Example 1

Quantification of *Neisseria gonorrhoeae* by the LAMP Method (1) Assay Template

Plasmid DNA was prepared as the internal standard material template via subcloning of part of the region of the cryptic plasmid of *Chlamydia trachomatis* (hereafter referred to as "CT plasmid"). Also, plasmid DNA was prepared as the target nucleic acid template via subcloning of part of the mtrA region of *Neisseria gonorrhoeae* (hereafter referred to as "NG plasmid").

```
Sequence of internal standard template
(CT plasmid):
                                        (SEQ ID NO: 1)
CTCGAGAAGA TTTATCGTAC GCAAATATCA TCTTTGCGGT    60
TGCGTGTCCT GTGACCTTCA

TTATGTCGGA GTCTGAGCAC CCTAGGCGTT TGTACTCCGT   120
CACAGCGGTT GCTCGAAGCA

CGTGCGGGGT TATCTTAAAA GGGATTGCAG CTTGTAGTCC   180
TGCTTGAGAG AACGTGCGGG

CGATTTGCCT TAACCCCACC ATTTTTCCGG AGCGAGTTAC   240
GAAGACAAAA CCTCTTCGTT

GACCGATGTA CTCTTGTAGA AAGTGCATAA ACTTCTGAGG   300
ATAAGTTATA ATAATCCTCT

TTTCTGTCTG ACGGTTCTTA AGCTGGGAGA AAGAAATGGT   360
AGCTTGTTGG AAACAAATCT

GACTAATCTC CAAGCTTAAG ACTTCAGAGG AGCGTTTACC   420
TCCTTGGAGC ATTGTCTGGG

CGATCAAC                                      428
```

(2) Synthesis of Internal Standard Primer and Quenching Probe

Primers targeting the region of the cryptic plasmid of *Chlamydia trachomatis* and having no cross-reactivity with related species were designed. Synthesis of primers was consigned to Operon Biotechnologies. Synthesis of quenching probes was consigned to J-Bio21.

CT-FIP:
(SEQ ID NO: 2)
5'-CAAGCAGGACTACAAGCTGCAGCGTTTGTACTCCGTCAC-3'

CT-BIP:
(SEQ ID NO: 3)
5'-GCGGGCGATTTGCCTTAACTCGGTCAACGAAGAGGTT-3'

CT-F3:
(SEQ ID NO: 4)
5'-ATGTCGGAGTCTGAGCAC-3'

CT-B3:
(SEQ ID NO: 5)
5'-CCTCAGAAGTTTATGCACTTTC-3'

CT-LF:
(SEQ ID NO: 6)
5'-AAGATAACCCCGCACGT-3'

CT-LB:
(SEQ ID NO: 7)
5'-GGAGCGAGTTACGAAGACA-3'

CT-Pr (TAMRA label):
(SEQ ID NO: 8)
5'-ATAACCCCGCACGTGCTTCGAGCAACC-3'

(3) Synthesis of Target Nucleic Acid Primer and Quenching Probe

Primers targeting the mtrA region of *Neisseria gonorrhoeae* and having no cross-reactivity with related species were designed. Synthesis of primers was consigned to Operon Biotechnologies. Synthesis of quenching probes was consigned to J-Bio21.

NG-FIP:
(SEQ ID NO: 9)
5'-CGTGGCTCAACACATGACCCAAGCGTCCGGTCGGCA-3'

NG-BIP:
(SEQ ID NO: 10)
5'-ACGGAGAAAGTTTACAACCGGACACAAAACAGGCTCATATCCAGC-3'

NG-F3:
(SEQ ID NO: 11)
5'-GCGGTTATCTCTGCATCG-3'

NG-B3:
(SEQ ID NO: 12)
5'-GGTGTCGTAGCGGAAAC-3'

NG-LF:
(SEQ ID NO: 13)
5'-CGGGAAAAATACAATATCGCCC-3'

NG-LB:
(SEQ ID NO: 14)
5'-CGACAAAACGGCACATTTATGG-3'

NG-Pr (BODIPY-FL label):
(SEQ ID NO: 15)
5'-CACATTTATGGTCAAACAGTGCGGCAAC-3'

(4) Composition and Concentration of LAMP Reaction Reagent

Concentrations of reagents in 30 μl of the final LAMP reaction solution were adjusted at the following levels.
30 mM Tris-HCl (pH 8.8)
15 mM KCl
15 mM $(NH_4)_2SO_4$
12 mM $MgSO_4$
0.15% Tween 20
2.1 mM dATP
2.1 mM dCTP
2.1 mM dGTP
2.1 mM dTTP
38.4 U Bst DNA polymerase (New England Biolab)
$10^7$ copies of CT plasmid
Internal standard primer
 0.8 μM CT-FIP (SEQ ID NO: 2) and CT-BIP (SEQ ID NO: 3)
 0.1 μM CT-F3 (SEQ ID NO: 4) and CT-B3 (SEQ ID NO: 5)
 0.4 μM CT-LF (SEQ ID NO: 6) and CT-LB (SEQ ID NO: 7)
0.067 μM internal standard probe CT-Pr (SEQ ID NO: 8)
Target nucleic acid primer
 0.8 μM NG-FIP (SEQ ID NO: 9) and NG-BIP (SEQ ID NO: 10)
 0.1 μM NG-F3 (SEQ ID NO: 11) and NG-B3 (SEQ ID NO: 12)
 0.4 μM NG-LF (SEQ ID NO: 13) and NG-LB (SEQ ID NO: 14)
0.067 μM target nucleic acid probe NG-Pr (SEQ ID NO: 15)

(5) Detection and Determination of Quantitative Value

Detection was carried out by the quenching probe method. Quenching of fluorescence caused by amplification of an internal standard material and a target nucleic acid was detected in real-time using an Mx3000P system (Stratagene). Quantitative values were determined based on the fact that the Tt value (the time for the fluorescent intensity varying upon amplification to reach a given level) depends on the initial template amount.

(6) Quantitative Evaluation of Target Nucleic Acid

A dilution series of $10^1$ to $10^7$ copies of NG plasmids were added to the LAMP reaction reagent as target nucleic acids. The LAMP reaction was carried out at 63° C. for 60 minutes, quenching of fluorescence was assayed in real-time by the quenching probe method, and a standard curve was prepared.

Figure 2:
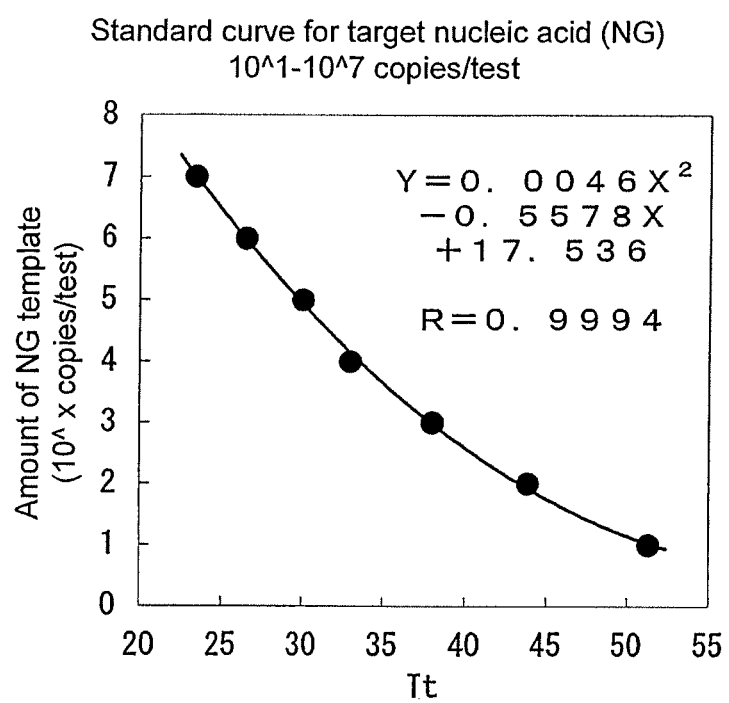
FIG. 2 is a chart showing a standard curve obtained using NG plasmid.
Figure 3:
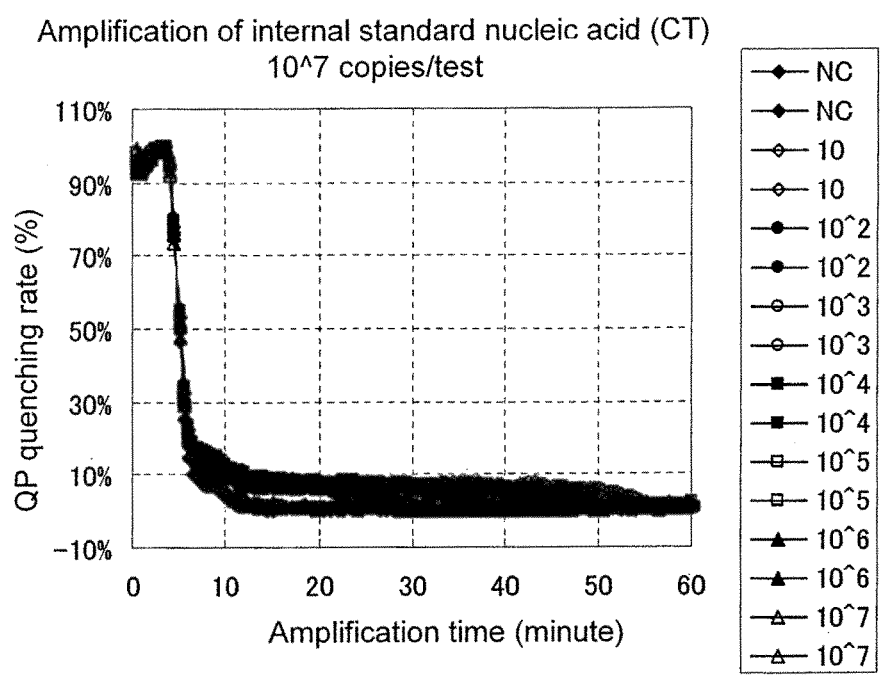
FIG. 3 is a chart showing the results attained via the LAMP method using a target nucleic acid (i.e., NG plasmid) at each concentration of $10^1$ to $10^7$ copies/test and an internal standard nucleic acid (i.e., CT plasmid) and assaying fluorescence quenching of a quenching probe caused along with amplification of an internal standard nucleic acid via Mx3000P real-time assay.

As a result, the minimum detection sensitivity was at 10 copies of NG plasmid per test (FIG. 1) and the range of quantitative assay was at $10^1$ to $10^7$ copies/test (with the standard curve exhibiting a correlation coefficient R of 0.9994) (FIG. 2). Good reproducibility was attained for both NG plasmids and CT plasmids (FIGS. 1 and 3) and all amplification procedures for $10^1$ to $10^7$ copies of NG plasmids per test were completed within 60 minutes.

Example 2

Quantification of HBV by the LAMP Method (1) Assay Template

Plasmid DNA was prepared via subcloning of an artificial nucleic acid as an internal standard material template (hereafter referred to as "Arita2 plasmid"). Also, plasmid DNA was prepared as the target nucleic acid template via subcloning of part of the HBV S region (hereafter referred to as "HBV plasmid").

Sequence of internal standard template
(Arita2 plasmid):
(SEQ ID NO: 16)
ATTCGAAGGG TGATTGGATC GGAGATAGGA TGGGTCAATC   60
GTAGGGACAA TCGAAGCCAG

AATGCAAGGG TCAATGGTAC GCAGAATGGA TGGCACTTAG   120
CTAGCCAGTT AGGATCCGAC

-continued

```
TATCCAAGCG TGTATCGTAC GGTGTATGCT TCGGAGTAAC    180
GATCGCACTA AGCATGGCTC

AATCCTAGGC TGATAGGTTC GCACATAGCA TGCCACATAC    240
GATCCGTGAT TGCTAGCGTG

ATTCGTACCG AGAACTCACG CCTTATGACT GCCCTTATGT    300
CACCGCTTAT GTCTCCCGAT

ATCACACCCG TTATCTCAGC CCTAATCTCT GCGGTTTAGT    360
CTGGCCTTAA TCCATGCCTC

ATAGCTACCC TCATACCATC GCTCATACCT TCCGACATTG    420
CATCCGTCAT TCCAACCCTG

ATTCCTACGG TCTAACCTAG CCTCTATCCT ACCCAGTTAG    480
GTTGCCTCTT AGCATCCCTG

TTACGTACGC TCTTACCATG CGTCTTACCT TGGCACTATC    540
GATGGGAGTA TGGTAGCGAG

TATGAACGG ACTAACGTAG GCAGTAAGCT AGGGTGTAAG     600
GTTGGGACTA AGGATGCCAG
```

(2) Synthesis of Internal Standard Primer and Quenching Probe

Primers targeting an artificial nucleic acid Arita2 were designed. Synthesis of primers was consigned to Operon Biotechnologies. Synthesis of quenching probes was consigned to J-Bio21.

Quenching probes (QP) are fluorescence-labeled probes that were developed by the National Institute of Advanced Industrial Science and Technology (AIST) based on the principle that a quenching probe hybridizes to a target sequence and fluorescence is quenched by guanine present on the target sequence (see JP Patent Nos. 3437816 and 3985959).

```
Arita2-FIP:
                                  (SEQ ID NO: 17)
5'-CGCTTGGATAGTCGGATGCAAGGGTCAATGGTAC-3'

Arita2-BIP:
                                  (SEQ ID NO: 18)
5'-ACGGTGTATGCTTCGGTGTGCGAACCTATCAGC-3'

Arita2-F3:
                                  (SEQ ID NO: 19)
5'-GGACAATCGAAGCCAGAA-3'

Arita2-B3:
                                  (SEQ ID NO: 20)
5'-ATCACGGATCGTATGTGG-3'

Arita2-LF:
                                  (SEQ ID NO: 21)
5'-GCTAGCTAAGTGCCATCC-3'

Arita2-LB:
                                  (SEQ ID NO: 22)
5'-AACGATCGCACTAAGCAT-3'

Arita2-Pr (TAMRA label):
                                  (SEQ ID NO: 23)
5'-GCTAGCTAAGTGCCATCCATTCTGCGTACC-3'
```

(3) Synthesis of Target Nucleic Acid Primer and Quenching Probe

Primers targeting the HBV S region were designed. Synthesis of primers was consigned to Operon Biotechnologies. Synthesis of quenching probes was consigned to J-Bio21.

```
HBV-FIP:
                                  (SEQ ID NO: 24)
5'-CCGCAGACACATCCAGCGATAAACCTCCAATCACTCACCAA-3'

HBV-BIP:
                                  (SEQ ID NO: 25)
5'-CATCCTGCTGCTATGCCTCATCTTCTTGTTCCTGGAATTAGAGG
ACA-3'

HBV-F3:
                                  (SEQ ID NO: 26)
5'-CAAAATTCGCAGTCCC-3'

HBV-B3:
                                  (SEQ ID NO: 27)
5'-GCAGGTCTTGCATGGTCC-3'

HBV-LF:
                                  (SEQ ID NO: 28)
5'-CAGCGATAGCCAGGACA-3'

HBV-LB:
                                  (SEQ ID NO: 29)
5'-TCTGGACTATCAAGGTATGTTGC-3'

HBV-Pr (BODIPY-FL label):
                                  (SEQ ID NO: 30)
5'-GTTGGTTCTTCTGGACTATCAAGGTATGTTGCCC-3'
```

(4) Composition and Concentration of LAMP Reaction Reagent

Concentrations of reagents in 30 μl of the final LAMP reaction solution were adjusted at the following levels.

25 mM Tris-HCl (pH 8.8)
12.8 mM KCl
12.8 mM $(NH_4)_2SO_4$
9.7 mM $MgSO_4$
0.10% Tween 20
1.79 mM dATP
1.79 mM dCTP
1.79 mM dGTP
1.79 mM dTTP
28.8 U Bst DNA polymerase (New England Biolab)
$10^6$ copies of Arita2 plasmid
Internal standard primer
    0.4 μM Arita2-FIP (SEQ ID NO: 17) and Arita2-BIP (SEQ ID NO: 18)
    0.05 μM Arita2-F3 (SEQ ID NO: 19) and Arita2-B3 (SEQ ID NO: 20)
    0.4 μM Arita2-LF (SEQ ID NO: 21) and Arita2-LB (SEQ ID NO: 22)
0.067 μM internal standard probe Arita2-Pr (SEQ ID NO: 23)
Target nucleic acid primer
    1.6 μM HBV-FIP (SEQ ID NO: 24) and HBV-BIP (SEQ ID NO: 25)
    0.2 μM HBV-F3 (SEQ ID NO: 26) and HBV-B3 (SEQ ID NO: 27)
    0.8 μM HBV-LF (SEQ ID NO: 28) and HBV-LB (SEQ ID NO: 29)
0.067 μM target nucleic acid probe HBV-Pr (SEQ ID NO: 30)

(5) Detection and Determination of Quantitative Value

Detection was carried out by the quenching probe method. Quenching of fluorescence caused by amplification of an internal standard material and a target nucleic acid was detected in real-time using an Mx3000P system (Stratagene). Quantitative values were determined based on the fact that the Tt value depends on the initial template amount.

(6) Quantitative Evaluation of Target Nucleic Acid

A dilution series of $10^1$ to $10^8$ copies of HBV plasmids were added to the LAMP reaction reagent as target nucleic acids. The LAMP reaction was carried out at 63° C. for 60 minutes, quenching of fluorescence was assayed in real-time by the quenching probe method, and a standard curve was prepared.

Figure 4:
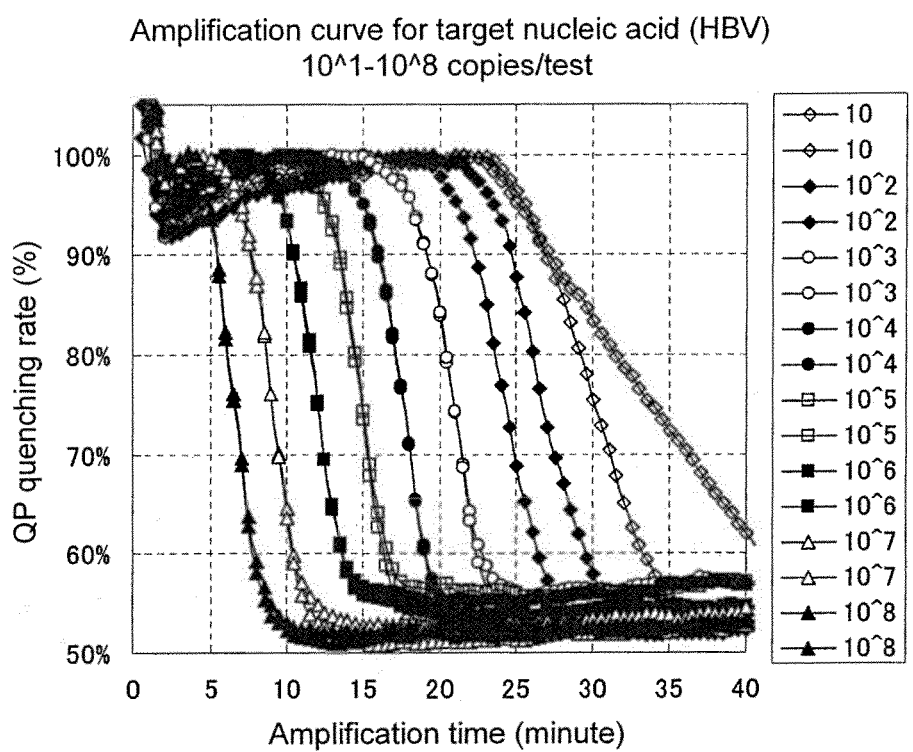
FIG. 4 is a chart showing the results attained via the LAMP method using a target nucleic acid (i.e. HBV plasmid) at each concentration of $10^1$ to $10^8$ copies/test and an internal standard nucleic acid (i.e., Arita2 plasmid) and assaying fluorescence quenching of a quenching probe caused along with amplification of the target nucleic acid via Mx3000P real-time assay.
Figure 5:
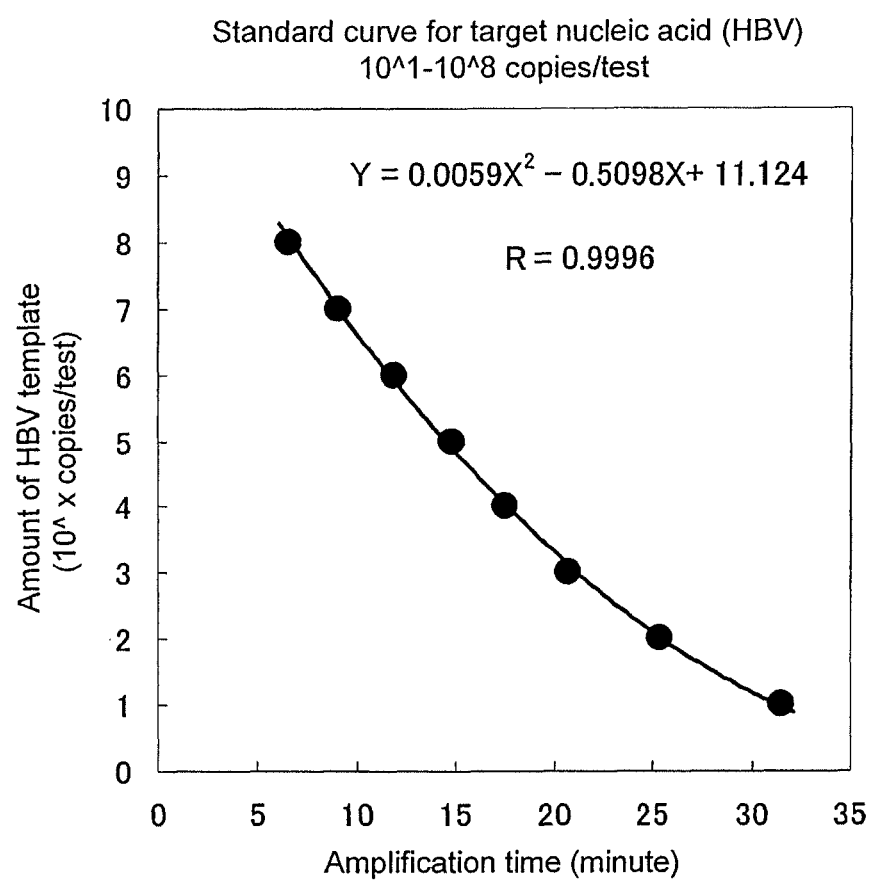
FIG. 5 is a chart showing a standard curve obtained using HBV plasmid.
Figure 6:
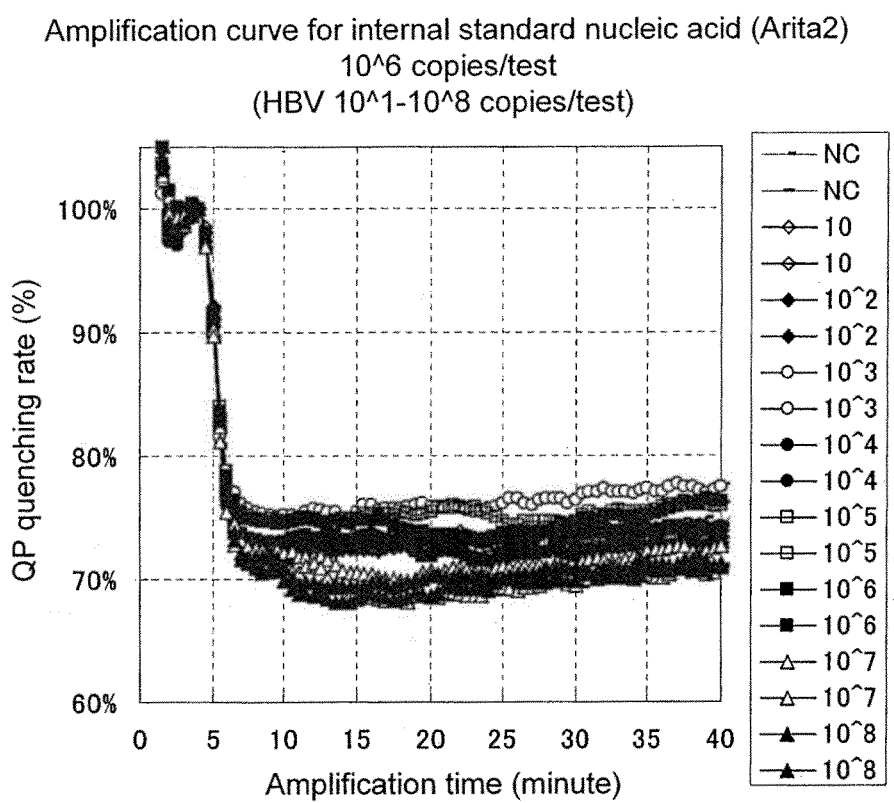
FIG. 6 is a chart showing the results attained via the LAMP method using a target nucleic acid (i.e., HBV plasmid) at each concentration of $10^1$ to $10^8$ copies/test and an internal standard nucleic acid (i.e., Arita2 plasmid) and assaying fluorescence quenching of a quenching probe caused along with amplification of an internal standard nucleic acid via Mx3000P real-time assay.

As a result, the minimum detection sensitivity was at 10 copies of HBV plasmids per test (FIG. 4) and the range of quantitative assay was between $10^1$ and $10^8$ copies/test (with the standard curve exhibiting a correlation coefficient R of 0.9996) (FIG. 5). Good reproducibility was attained for both HBV plasmids and Arita2 plasmids (FIGS. 4 and 6) and all amplification procedures for $10^1$ to $10^8$ copies of HBV plasmids per test were completed within 60 minutes.

Example 3

Influence of Changes in Concentration of Internal Standard Material on HBV Detection In order to inspect concentration of the internal standard material necessary for preceding amplification, the amounts of the internal standard material (Arita2 plasmid) templates were determined to be $10^2$ copies, $10^4$ copies, or $10^6$ copies per test in HBV detection.

(1) Composition and Concentration of LAMP Reaction Reagent

The composition and concentration of the reaction reagent employed in Example 2 were utilized, except for the amount of the internal standard material template.

(2) Amount of HBV Plasmid Template and Detection Thereof

The amounts of HBV plasmid templates were set at two levels; i.e., $10^1$ copies and $10^8$ copies thereof per test, and the LAMP reaction was carried out at 63° C. for 60 minutes. Quenching of fluorescence for each amount of template caused by amplification of HBV plasmids and an internal standard material (Arita2 plasmid) was detected in real-time using an Mx3000P system (Stratagene), and the Tt value was determined.

(3) Results

Figure 7:
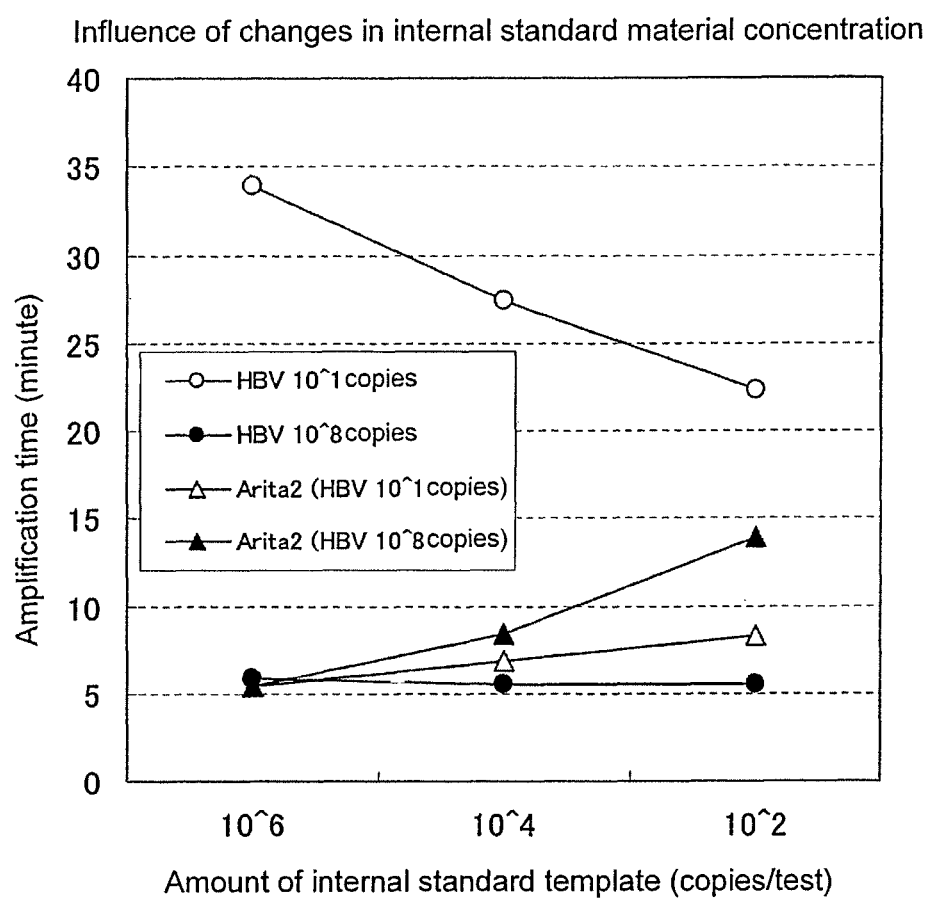
FIG. 7 is a chart showing changes in amplification times for a target nucleic acid (HBV plasmid) and an internal standard nucleic acid (Arita2 plasmid) at internal standard material template concentrations of $10^2$, $10^4$, and $10^6$ copies/test.

The Tt value determined in (2) is shown in Table 1 and in FIG. 7 as amplification time. When concentration of the internal standard material was low (i.e., $10^2$ copies/test), the highly concentrated HBV plasmid template ($10^8$ copies/test) was amplified before the internal standard material was amplified. As a consequence, the amplification reaction of the internal standard material was significantly delayed. The difference in the amplification time for the internal standard materials between HBV plasmid templates at two different concentrations was as large as 5.67 minutes. When concentration of the internal standard material was high (i.e., $10^6$ copies/test), the amplification reaction of the internal standard material was not delayed, and amplification times for the internal standard materials were substantially constant, regardless of concentrations of HBV plasmid templates. In order to rapidly amplify the internal standard material within a given period of time regardless of the amount of the target nucleic acid template, accordingly, it is necessary to set the amount of the internal standard material template at a high level. In the present case, it is adequate to select an amount of $10^6$ copies/test.

TABLE 1

Amplification time for target nucleic acid and internal standard material for each amount of internal standard material template (min)

| | Amount of internal standard template (copies/test) | | |
|---|---|---|---|
| Amount of template (copies/test) | $10^6$ | $10^4$ | $10^2$ |
| $10^1$ copies of HBV | 33.9 | 27.4 | 22.4 |
| $10^8$ copies of HBV | 5.90 | 5.57 | 5.54 |
| Arita2 ($10^1$ copies of HBV) | 5.38 | 6.84 | 8.33 |
| Arita2 ($10^8$ copies of HBV) | 5.41 | 8.41 | 14.0 |

Example 4

Influence of Changes in Concentration of Internal Standard Primer on HBV Detection The concentration of the internal standard primer suitable for preceding amplification was inspected by changing concentrations of the internal standard primer to ×1 (i.e., concentration employed in a system that does not perform preceding amplification of an internal standard material), ×0.25, ×0.3, and ×0.5 at the time of HBV detection.

(1) Composition and Concentration of LAMP Reaction Reagent

×1 internal standard primer 1.3 µM Arita2-FIP (SEQ ID NO: 17) and Arita2-BIP (SEQ ID NO: 18)

0.17 µM Arita2-F3 (SEQ ID NO: 19) and Arita2-B3 (SEQ ID NO: 20)

1.3 µM Arita2-LF (SEQ ID NO: 21) and Arita2-LB (SEQ ID NO: 22)

The composition and concentration of the reaction reagent employed in Example 2 were employed, except for the amount of the internal standard primer.

(2) Amount of HBV Plasmid Template and Detection Thereof

The amounts of HBV plasmid templates were set at two levels; i.e., $10^1$ copies and $10^8$ copies thereof per test, and the LAMP reaction was carried out at 63° C. for 60 minutes. Quenching of fluorescence for each amount of template caused by amplification of HBV plasmids and an internal standard material was detected in real-time using an Mx3000P system (Stratagene), and the Tt value was determined.

(3) Results

Figure 8:
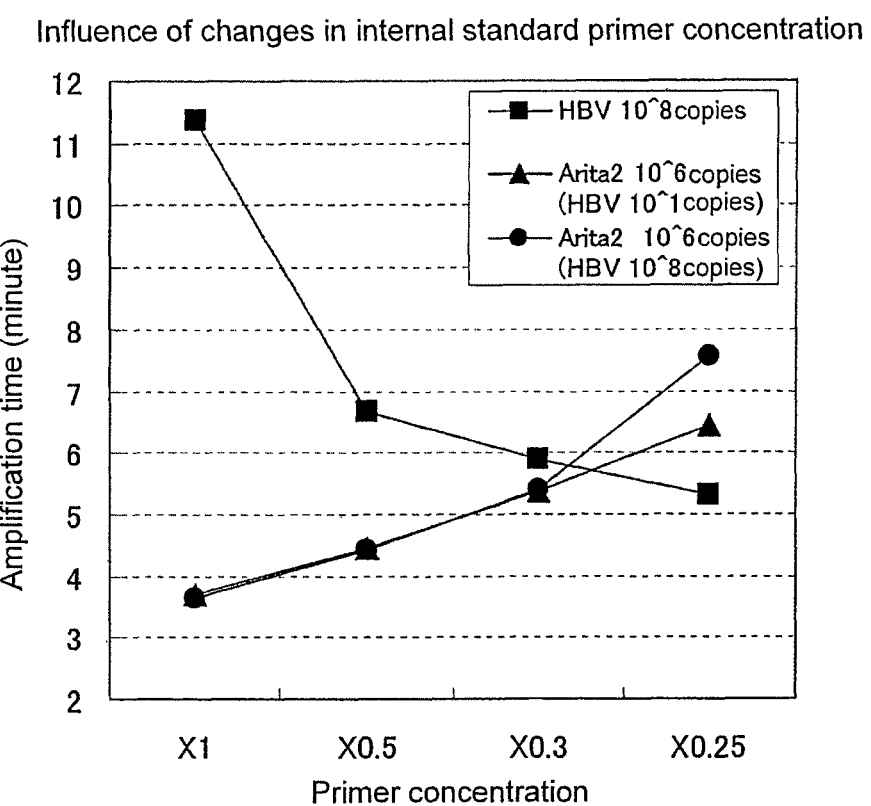
FIG. 8 is a chart showing changes in amplification times for a target nucleic acid (HBV plasmid) and an internal standard nucleic acid (Arita2 plasmid) using an internal standard primer at concentration of ×1 and primers at lower concentration (×0.25, ×0.3, and ×0.5).

The Tt value determined in (2) is shown in Table 2 and in FIG. 8 as amplification time. When the amount of the internal standard primer was large (×1), the amplification time for HBV plasmid became long as a whole, and a delay in the amplification time around the detection sensitivity level was significant. If the amount of the internal standard primer was excessively reduced (×0.25), the amplification time for the internal standard material changed due to the concentration of HBV plasmid, and it was difficult to complete the amplification reaction within the given period of time. In the present case, accordingly, it is adequate to select an internal standard primer concentration of ×0.3.

TABLE 2

Amplification time for target nucleic acid and internal standard material for each amount of internal standard primer (min)

| Amount of template (copies/test) | Amount of internal standard primer | | | |
|---|---|---|---|---|
| | +331 | ×0.5 | ×0.3 | ×0.25 |
| $10^1$ copies of HBV | 52.6 | 34.2 | 33.9 | 21.3 |
| $10^8$ copies of HBV | 11.4 | 6.7 | 5.9 | 5.3 |
| $10^6$ copies of Arita2 ($10^1$ copies of HBV) | 3.70 | 4.45 | 5.38 | 6.45 |
| $10^6$ copies of Arita2 ($10^8$ copies of HBV) | 3.65 | 4.43 | 5.41 | 7.57 |

Example 5

Influence of Concentration of Reaction Reagent Components on HBV Detection

Concentrations of the reaction reagent components suitable for preceding amplification of an internal standard material were inspected by changing concentrations of the reaction reagent components including substrate nucleotides at the time of HBV detection, and the influence thereof was inspected.

(1) Composition and Concentration of LAMP Reaction Reagent

A reagent component A×1 including substrate nucleotides (at a concentration that is generally employed in a single target nucleic acid detection system) and a reagent component ×1.2, which is a 1.2-fold concentrate of A×1, were prepared.

Reaction component A×1

Concentrations of reagents in 30 μl of the final LAMP reaction solution are set at the levels shown below.
25 mM Tris-HCl (pH 8.8)
10 mM KCl
10 mM $(NH_4)_2SO_4$
8 mM $MgSO_4$
0.10% Tween 20
1.4 mM dATP
1.4 mM dCTP
1.4 mM dGTP
1.4 mM dTTP
28.8 U Bst DNA polymerase (New England Biolab)

The internal standard material (Arita2 plasmid), the internal standard primer, the internal standard probe, the target nucleic acid primer, and the target nucleic acid probe, except for reagent component A, and the concentrations thereof employed in Example 2 were employed herein.

(2) Amount of HBV Plasmid Template and Detection Thereof

The amounts of HBV plasmid templates were set at three levels; i.e., $10^1$ copies, $10^4$ copies, and $10^8$ copies thereof per test, and the LAMP reaction was carried out at 63° C. for 60 minutes. Quenching of fluorescence for each amount of template caused by amplification of HBV plasmids and an internal standard material was detected in real-time using an Mx3000P system (Stratagene), and the Tt value was determined.

(3) Results

Figure 9:
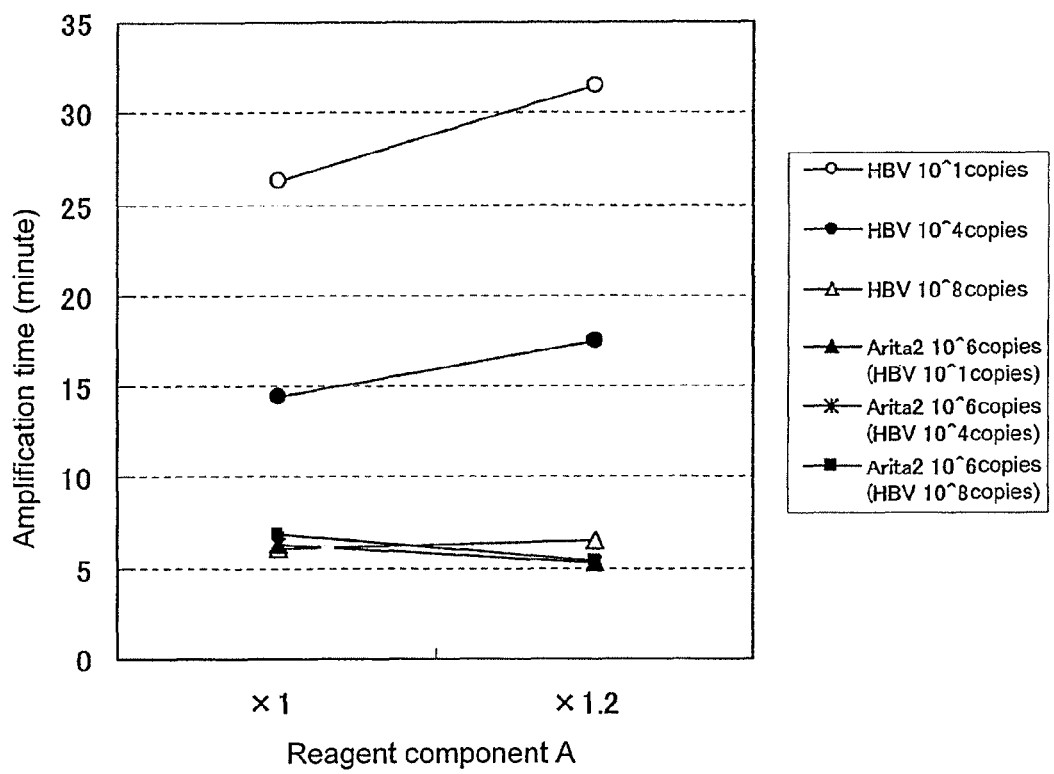
FIG. 9 is a chart showing changes in amplification times for a target nucleic acid (HBV plasmid) and an internal standard nucleic acid (Arita2 plasmid) with the use of a reagent component A×1 and a reagent component A×1.2 of high concentration.

The Tt value determined in (2) is shown in Table 3 and in FIG. 9 as amplification time. When the reaction solution of reagent component A×1 was used, a highly concentrated HBV plasmid template ($10^8$ copies/test) was amplified before the internal standard material was amplified. When the ×1.2 reaction solution was used, however, the internal standard material was first amplified, and the internal standard material was amplified within a given period of time, regardless of concentration of HBV plasmid template.

Thus, it is preferable to set concentration of a reaction reagent component including substrate nucleotides at a higher level, in order to perform preceding amplification of an internal standard material. In the present case, a concentration of ×1.2 is adequate.

TABLE 3

Amplification time (minute) for target nucleic acid and internal standard material for each amount of reaction reagent component

| | Reagent component A | |
|---|---|---|
| Amount of template (copies/test) | ×1 | ×1.2 |
| $10^1$ copies of HBV | 26.3 | 31.5 |
| $10^4$ copies of HBV | 14.4 | 17.5 |
| $10^8$ copies of HBV | 6.10 | 6.50 |
| Arita2 $10^6$ ($10^1$ copies of HBV) | 6.33 | 5.35 |
| Arita2 $10^6$ ($10^4$ copies of HBV) | 6.36 | 5.26 |
| Arita2 $10^6$ ($10^8$ copies of HBV) | 6.83 | 5.43 |

Example 6

Detection of *Neisseria gonorrhoeae* by the LAMP Method (1) Composition and Concentration of LAMP Reaction Reagent The composition and concentration of the reaction reagent employed in Example 1 were employed herein.

(2) Detection

The LAMP reaction was carried out at 63° C. for 60 minutes by designating high-concentration NG plasmid or low-concentration NG plasmid as the target nucleic acid, and quenching of fluorescence was detected in real-time by the quenching probe method.

(3) Result

Figure 10:
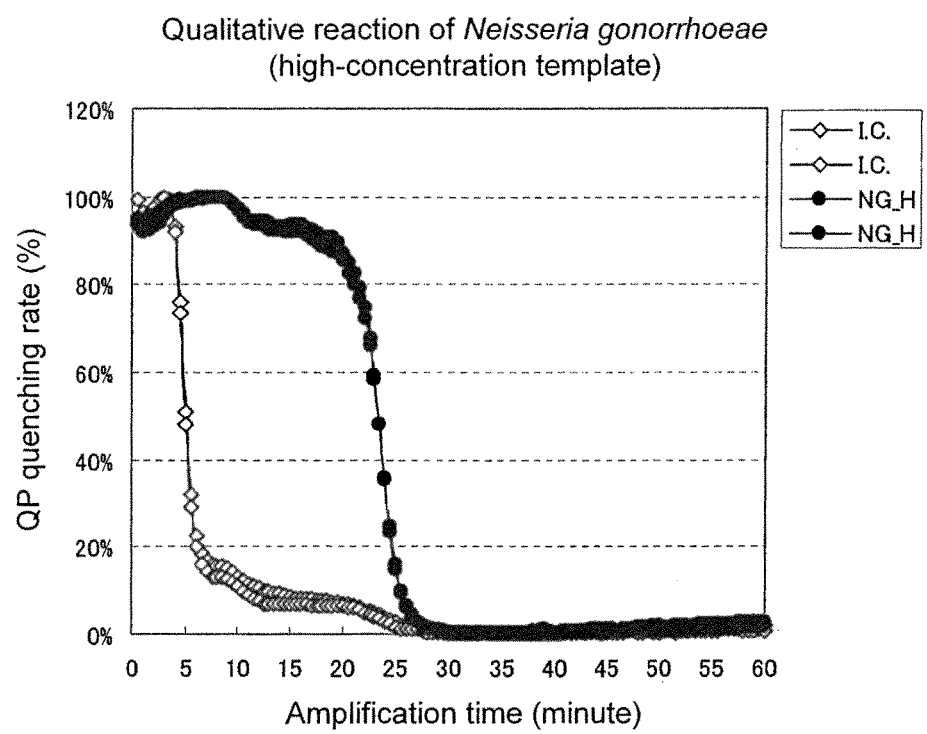
FIG. 10 is a chart showing the results of amplification of an internal standard nucleic acid (CT plasmid; I.C.) and a high-concentration template of NG plasmid (NG_H) in the same reaction solution.
Figure 11:
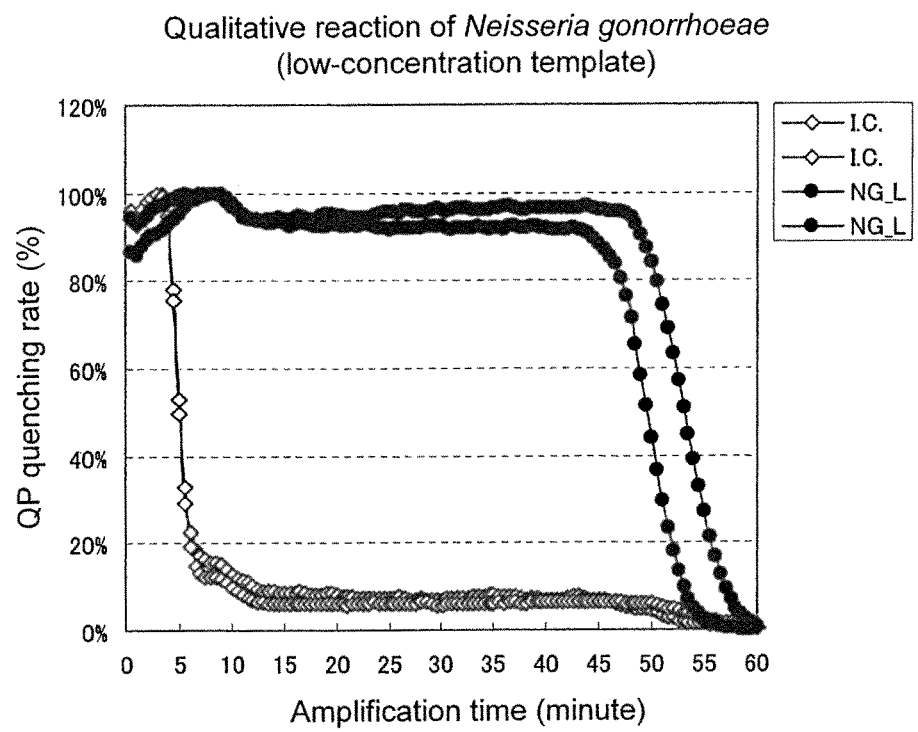
FIG. 11 is a chart showing the results of amplification of an internal standard nucleic acid (CT plasmid; I.C.) and a low-concentration template of NG plasmid (NG_L) in the same reaction solution.

As shown in FIGS. 10 and 11, the internal standard material (CT plasmid) and the target nucleic acid (NG plasmid) could be amplified in the same reaction system, and the amplification time for the internal standard material was constant, regardless of concentrations of target nucleic acid templates.

All publications, patents, and patent applications cited herein are incorporated herein by reference in their entirety.

The invention claimed is:

1. A method for nucleic acid amplification using an internal standard material, comprising:

amplifying a target nucleic acid; and amplifying the internal standard material;

wherein amplifying the target nucleic acid and amplifying the internal standard material occur under isothermal conditions in a same reaction solution, wherein the amplifying of the internal standard material is initiated prior to initiating the amplifying of the target nucleic acid, thereby reducing the influence of the amplified internal standard material on the amplifying of the target nucleic acid;

wherein the internal standard material has a nucleotide sequence different from that of the target nucleic acid at least in the primer design region;

wherein the oligonucleotide primer used for amplifying the internal standard material specifically hybridizes to the internal standard material but does not specifically hybridize to the target nucleic acid, and the oligonucleotide primer for amplifying the target nucleic acid specifically hybridizes to the target nucleic acid but does not specifically hybridize to the internal standard material;

wherein the oligonucleotide primer for amplifying the internal standard material initiates amplifying the internal standard material earlier than the initiation of amplification of the target nucleic acid.

2. The method according to claim 1, comprising the following steps of:

(a) adding a solution containing an internal standard material with a known concentration or copy number to a sample containing a target nucleic acid;

(b) performing an amplification reaction using an amplification reaction solution containing an oligonucleotide primer used for amplification of the internal standard material that allows initiation of amplification of an internal standard material prior to initiation of amplification of a target nucleic acid and an oligonucleotide primer used for amplification of a target nucleic acid;

(c) performing assay via a means that allows the amplification reaction of the internal standard material to be distinguished from the amplification reaction of the target nucleic acid; and (d) detecting the presence or absence of a target nucleic acid or quantifying the target nucleic acid.

3. The method according to claim 1, comprising the following steps of:

(a) adding a solution containing an internal standard material with a known concentration or copy number to a sample containing a target nucleic acid;

(b) performing an amplification reaction using an amplification reaction solution containing an oligonucleotide primer used for amplification of an internal standard material that allows initiation of amplification of an internal standard material prior to initiation of amplification of a target nucleic acid and an oligonucleotide primer used for amplification of a target nucleic acid;

(c) performing real-time assay via a means that allows the amplification reaction of the internal standard material to be distinguished from the amplification reaction of the target nucleic acid, and determining the initial concentration or copy number of the target nucleic acid in a sample based on the results of assay and the amount of the internal standard material added; and, (d) detecting the presence or absence of a target nucleic acid or quantifying the target nucleic acid.

4. The method for nucleic acid amplification according to any one of claims 1 to 3, wherein the internal standard material is amplified before the target nucleic acid is amplified under the following conditions:

(a) the concentration of an internal standard material is set to be higher and/or the concentration of the oligonucleotide primer used for amplification of an internal standard material is set lower than those of an amplification reaction solution used for an assay involving simultaneous amplification of an internal standard material and the target nucleic acid; and/or (b) the concentration of substrate nucleotide is set to be higher than that of an amplification reaction solution used for an assay involving amplification of the same target nucleic acid without using an internal standard material.

5. The method for nucleic acid amplification according to any one of claims 1 to 3, wherein the amplification reaction involves the use of primer (a) and/or (b):

(a) when a first arbitrary sequence F1c and a second arbitrary sequence F2c are successively selected from the 3' side of the target sequence of a template nucleic acid toward the 3' terminal on the template nucleic acid, a primer comprising a sequence identical to F1c and a sequence F2 complementary to F2c in that order from the 5' side toward the 3' side; and (b) when a third arbitrary sequence R1 and a fourth arbitrary sequence R2 are successively selected from the 5' side of the target sequence of a template nucleic acid toward the 5' terminal on the template nucleic acid, a primer comprising a sequence R1c complementary to R1 and a sequence R2 identical to R2 in that order from the 5' side toward the 3' side.

6. The method according to any one of claims 1 to 3, wherein the amplification reaction is the LAMP method.

7. The method of claim 4, wherein the substrate nucleotide comprises a deoxyribonucleotide triphosphate.

* * * * *

SEQUENCE LISTING

<160> NUMBER OF SEQ ID NOS: 30

<210> SEQ ID NO 1
<211> LENGTH: 428
<212> TYPE: DNA
<213> ORGANISM: Artificial Sequence -continued

```
<220> FEATURE:
<223> OTHER INFORMATION: Description of Artificial Sequence:synthetic
      DNA

<400> SEQUENCE: 1
ctcgagaaga tttatcgtac gcaaatatca tctttgcggt tgcgtgtcct gtgaccttca      60
ttatgtcgga gtctgagcac cctaggcgtt tgtactccgt cacagcggtt gctcgaagca    120 cgtgcgggt tatcttaaaa gggattgcag cttgtagtcc tgcttgagag aacgtgcggg     180
cgatttgcct taacccccac cttttttccgg agcgagttac gaagacaaaa cctcttcgtt    240
gaccgatgta ctcttgtaga aagtgcataa acttctgagg ataagttata ataatcctct    300
tttctgtctg acggttctta agctgggaga agaaatggt agcttgttgg aaacaaatct     360
gactaatctc caagcttaag acttcagagg agcgtttacc tccttggagc attgtctggg    420
cgatcaac                                                             428

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 2
caagcaggac tacaagctgc agcgtttgta ctccgtcac                             39

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 3
gcgggcgatt tgccttaact cggtcaacga agaggtt                               37

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 4
atgtcggagt ctgagcac                                                    18

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 5
cctcagaagt ttatgcactt tc                                               22

<210> SEQ ID NO 6
<211> LENGTH: 17
<212> TYPE: DNA
<213> ORGANISM: Artificial Sequence
<220> FEATURE:
```

```
<223> OTHER INFORMATION: Description of Artificial Sequence:synthetic
      DNA

<400> SEQUENCE: 6
aagataaccc cgcacgt                                                  17

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 7
ggagcgagtt acgaagaca                                                19

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 8 ataacccgc acgtgcttcg agcaacc                                        27

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 9
cgtggctcaa cacatgaccc aagcgtccgg tcggca                             36

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 10
acggagaaag tttacaaccg gacacaaaac aggctcatat ccagc                   45

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 11
gcggttatct ctgcatcg                                                 18

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:synthetic
      DNA
```

<400> SEQUENCE: 12
ggtgtcgtag cggaaac                                                     17

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 13
cgggaaaaat acaatatcgc cc                                               22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 14
cgacaaaacg gcacatttat gg                                               22

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 15
cacatttatg gtcaaacagt gcggcaac                                         28

<210> SEQ ID NO 16
<211> LENGTH: 600
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 16
attcgaaggg tgattggatc ggagatagga tgggtcaatc gtagggacaa tcgaagccag      60
aatgcaaggg tcaatggtac gcagaatgga tggcacttag ctagccagtt aggatccgac     120
tatccaagcg tgtatcgtac ggtgtatgct tcggagtaac gatcgcacta agcatggctc     180
aatcctaggc tgataggttc gcacatagca tgccacatac gatccgtgat tgctagcgtg     240
attcgtaccg agaactcacg ccttatgact gcccttatgt caccgcttat gtctcccgat     300
atcacacccg ttatctcagc cctaatctct gcggtttagt ctggccttaa tccatgcctc     360
atagctaccc tcataccatc gctcataacct tccgacattg catccgtcat tccaaccctg    420
attcctacgg tctaacctag cctctatcct acccagttag gttgcctctt agcatccctg     480
ttacgtacgc tcttaccatg cgtcttacct tggcactatc gatgggagta tggtagcgag     540
tatggaacgg actaacgtag gcagtaagct agggtgtaag gttgggacta aggatgccag     600

<210> SEQ ID NO 17
<211> LENGTH: 34
<212> TYPE: DNA
<213> ORGANISM: Artificial Sequence

```
<220> FEATURE:
<223> OTHER INFORMATION: Description of Artificial Sequence:synthetic
      DNA

<400> SEQUENCE: 17
cgcttggata gtcggatgca agggtcaatg gtac                              34

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 18
acggtgtatg cttcggtgtg cgaacctatc agc                               33

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 19
ggacaatcga agccagaa                                                18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 20
atcacggatc gtatgtgg                                                18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 21
gctagctaag tgccatcc                                                18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 22
aacgatcgca ctaagcat                                                18

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:synthetic
```

-continued

DNA

<400> SEQUENCE: 23
gctagctaag tgccatccat tctgcgtacc                                      30

<210> SEQ ID NO 24
<211> LENGTH: 41
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 24
ccgcagacac atccagcgat aaacctccaa tcactcacca a                         41

<210> SEQ ID NO 25
<211> LENGTH: 47
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 25
catcctgctg ctatgcctca tcttcttgtt cctggaatta gaggaca                   47

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 26
caaaattcgc agtccc                                                     16

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 27
gcaggtcttg catggtcc                                                   18

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 28
cagcgatagc caggaca                                                    17

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence:synthetic
      DNA

```
<400> SEQUENCE: 29
tctggactat caaggtatgt tgc                                       23

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 30
gttggttctt ctggactatc aaggtatgtt gccc                           34
```